United States Patent [19]
Eden et al.

[11] Patent Number: 5,139,627
[45] Date of Patent: * Aug. 18, 1992

[54] CORROSION MONITORING

[75] Inventors: David A. Eden; David G. John; John L. Dawson, all of Manchester, England

[73] Assignee: Capcis Limited, Manchester, England

[*] Notice: The portion of the term of this patent subsequent to Oct. 18, 2007 has been disclaimed.

[21] Appl. No.: 272,693

[22] PCT Filed: May 11, 1987

[86] PCT No.: PCT/GB87/00310
  § 371 Date: Nov. 14, 1990
  § 102(e) Date: Nov. 14, 1990

[87] PCT Pub. No.: WO87/07022
  PCT Pub. Date: Nov. 19, 1987

[30] Foreign Application Priority Data

May 12, 1986 [GB] United Kingdom ............... 8611518

[51] Int. Cl.$^5$ ........................................... G01N 17/02
[52] U.S. Cl. ................................. 204/153.11; 204/404
[58] Field of Search ........................... 204/153.11, 404

[56] References Cited

U.S. PATENT DOCUMENTS

| | | | |
|---|---|---|---|
| 3,660,249 | 5/1972 | Townsend | 204/153.11 |
| 3,878,064 | 4/1975 | Weisstuch et al. | 204/153.11 |
| 4,238,298 | 12/1980 | Tsuru et al. | 204/153.11 |
| 4,395,318 | 7/1983 | Tait et al. | 204/404 |
| 4,575,678 | 3/1986 | Hladky | 324/425 |

Primary Examiner—Aaron Weisstuch
Attorney, Agent, or Firm—Spensley, Horn, Jubas & Lubitz

[57] ABSTRACT

A method and apparatus for detecting and measuring localized corrosion of a metallic surface is described. An array of electrodes fabricated from the same material as the metallic surface is exposed to the same corrosion conditions as the metallic surface. The coupling current between two electrodes of the array is measured, and the electrochemical current noise originating in the electrode array is measured. The two measurements are compared, the electrochemical current noise increasing as compared to the coupling current as the degree to which corrosion is localized increases. The electrochemical current noise originating in the coupled array electrode and the associated electrochemical corrosion potential noise are produced by the natural corrosion processes. The corrosion current is measured by comparison or correlation of the electrochemical current noise and the electrochemical potential noise, the electrochemical potential being measured by means of a third electrode in the array, a reference electrode or a relatively inert electrode. Comparison or correlation of the electrochemical potential noise to the electrochemical current noise provides a resistive noise or impedance, which is inversely proportional to the corrosion current. The corrosion measurement or metal penetration rate is then obtained from the measured corrosion current, as provided by the resistive noise or impedance noise determination, but modified by the degree of localization, as measured by the electrochemical current noise and coupling current determinations.

6 Claims, 1 Drawing Sheet

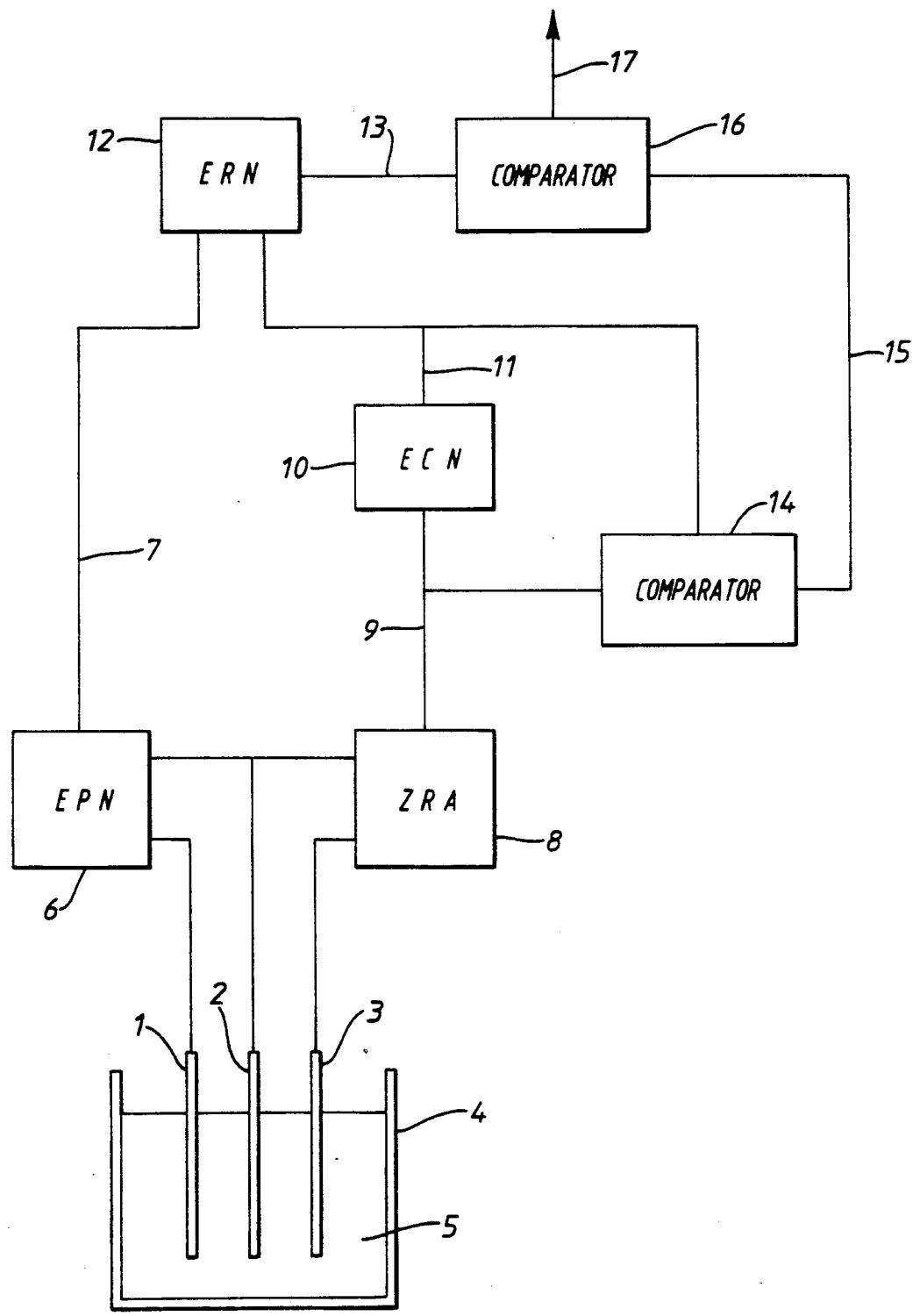

CORROSION MONITORING

The present invention relates to corrosion monitoring.

It is known that corrosion is an electrochemical phenomena, and as such, measurements of electrochemical parameters associated with corrosion processes may be used to estimate the rate of corrosion attack. Methods which have been used in the past and are known and well documented include the linear polarisation resistance method in which a dc signal is applied to a corroding cell consisting of two or three electrodes and the resulting dc polarisation is monitored. Provided the applied current is small so that the potential shift is less than 20 mV the response is linear in most cases and the measured resistance (termed the polarisation resistance) may be related inversely to the rate of the uniform corrosion attack. Other techniques include the application of electrochemical impedance in which a sine wave current is applied, in a similar manner to the linear polarisation technique, and the sine wave potential resulting from the applied current is monitored. Alternatively, a pseudo-random noise signal can be applied and the electrochemical impedance obtained by time domain transformations. Again, provided the current is small enough such that the resulting cell potential shift is not more than $\pm 20$ mV, the response is linear. Corrosion includes capacitive components, and therefore if the frequency of the applied signal is varied the resulting output signal is also varied: hence by inputting a range of frequencies a range of outputs may be obtained and these may be suitably analysed to provide information corresponding to the solution resistance, the corrosion kinetics and other aspects including electrochemical double layer capacity, diffusion effects and absorption of intermediates on the surface. The corrosion rate is then estimated by use of the calculated charge transfer resistance from the electrochemical impedance data in a manner essentially the same as for linear polarisation resistance.

Both the above electrochemical techniques, whilst widely used, suffer severe limitations in that they can only provide information on uniform corrosion conditions, that is by their very nature they provide an average signal for the surface of the electrodes being monitored. However, depending upon the type of environment, the metallic material and type of corrosion occurring, it is often found that the assumption that the corrosion rate is proportional to the measured charge transfer or polarisation resistance is invalid since the corrosion is of a localised nature. A further complication arises from the interference effect of solution resistance which may be variable during the measurement period or of a high value thereby altering the observed measurements In order to overcome the above limitations the use of electrochemical noise analysis has been applied and shown to be successful particularly for localised corrosion involving breakdown of a passive film. Essentially, electrochemical noise analysis consists of the measurement and analysis of small frequency, small amplitude random fluctuations in the corrosion potential of a corroding electrode. Suitable analysis is by means of frequency response analysis using Fast Fourier Transforms or Maximum Entropy Spectral Analysis, or by suitable filtering of the signal through a band pass system centred at 50 mHz$\pm$10 mHz and the subsequent calculation of the root mean square of the filtered signal. U.S. Pat. No. 4,575,678 describes such techniques. Previous experience has shown that this analysis may yield information as to both corrosion type and corrosion rate.

Another electrochemical measurement system which has been successfully applied in corrosion studies is the monitoring of coupling currents between dissimilar electrodes, for example, copper and steel electrodes, for measurement of corrosion phenomena. However, useful information can be obtained using similar electrodes of identical material, particularly when the system is moving from a general to a localised corrosion form of attack. In this instance two similar electrodes immersed in a conductive media are coupled via a zero resistance ammeter (null impedance ammeter). Such a system enables the current flowing in the network to be determined whilst imparting substantially zero resistance to the current path. Experience has shown that in cases where pitting corrosion occurs, one electrode will preferentially become anodic (that is it will pit) whilst the other electrode will become preferentially cathodic (that is provide an increased current to maintain the pitting of the other electrode). The degree or otherwise of discontinuity between the two electrodes may be related to the extent of corrosion. The method is therefore useful in identifying when corrosion changes from uniform to localised corrosion. With uniform corrosion conditions, the corrosion current may be related to the mean coupling current $I_{mean}$ by the following:

$$I_{corr} = k_1 I_{mean}$$

where $k_1$ is a system related constant

Also, by combining the coupling current analysis with electrochemical noise analysis further information may be obtained. For example, two similar electrodes are coupled together via a zero resistance ammeter and the output of the zero resistance ammeter is then passed to the input of the electrochemical noise analysis system. In this way the fluctuation of the coupling current may be analysed in essentially a similar manner as for electrochemical potential noise analysis described previously. By suitable configuration of electrodes and analysis equipment it is possible to obtain simultaneously both electrochemical potential noise data and coupling current data and electrochemical current noise data. Experience has shown that the rms or standard deviation values of both the electrochemical potential noise (termed $V_n$) and the electrochemical current noise (termed $I_n$) can be related using Ohm's law to produce a resistance noise value (termed $R_n$) as the frequency approaches zero Hz. Alternatively the impedance (termed $|Z_n|$) may be described as a function of frequency by means of correlation of $I_n$ and $V_n$ using frequency response analysis. This value appears to be related to the corrosion rate and has been considered as analogous to both the charge transfer resistance and polarisation resistance, as noted previously.

It is an object of the present invention to provide a method and apparatus for improving the accuracy with which the type of corrosion attacking a particular metallic material can be assessed.

According to the present invention there is provided an apparatus for detecting localised corrosion of a metallic surface, comprising an array of two or more electrodes fabricated from the same material as the metallic surface and exposed to the same corrosion conditions as the metallic surface, means for measuring the coupling current between two or more electrodes of the array, means for measuring electrochemical current noise originating in the electrode array, and means for comparing the coupling current with the electrochemical current noise to provide an output indicative of the degree to which corrosion is localised.

The greater the electrochemical current noise as compared to the coupling current, the greater is the degree to which corrosion is localised.

Preferably, the apparatus also comprises means for measuring the electrochemical potential noise originating in the electrode array, means for correlating the electrochemical potential noise and the electrochemical current noise to provide a resistive/impedance noise related output, and means for comparing the said output indicative of the degree to which corrosion is localised with the resistive/impedance noise output to provide an output indicative of the rate of localised corrosion.

The present invention also provides a method for detecting localised corrosion of a metallic surface, wherein an array of electrodes fabricated from the same material as the metallic surface is exposed to the same corrosion conditions as the metallic surface, the coupling current between two electrodes of the array is measured, electrochemical current noise originating in the electrode array is measured, and the coupling current is compared with the electrochemical current noise.

The present invention is particularly useful for detecting corrosion resulting in the formation of pits, but can also be used to detect other forms of localised corrosion, for example stress corrosion cracking, or crevice attack Furthermore, variations in the ratio between coupling current and electrochemical current noise is also indicative of changes occurring in corrosion processes. Such changes can occur for example when the chemical composition of a fluid to which the electrodes are exposed varies, and detection of such changes makes it possible to assess the affects on corrosion processes of adjustments to the operation of the system being monitored.

An apparatus providing outputs suitable for use in accordance with the present invention is illustrated in the attached drawing.

Referring to that drawing, three electrodes 1, 2 and 3 are positioned so as to be exposed to the same corrosion conditions as a metallic surface (not shown) the corrosion of which is to be monitored. In the drawing these conditions are indicated by a tank 4 filled with a corrosive liquid 5.

Electrodes 1 and 2 are connected to an electrochemical potential noise monitoring apparatus 6 which provides on output 7 an output signal representative of $V_n$, that is the rms or standard deviation of the potential noise The electrochemical potential noise may be monitored as shown by a circuit connected between the coupled electrodes 2 and 3 and a third electrode 1 of the array. A reference electrode or relatively inert electrode could be used rather than the third electrode of the array. A zero resistance ammeter 8 is connected across electrodes 2 and 3 and produces on output 9 an output signal corresponding to $I_{mean}$, that is the dc coupling current.

The output 9 is connected to an electrochemical current noise measuring apparatus 10 which provides on output 11 an output signal corresponding to $I_n$, that is the rms or standard deviation of the current noise. The outputs 7 and 11 are applied to a circuit 12 for comparing the electrochemical potential noise and the electrochemical current noise. The circuit 12 provides on output 13 an output signal $R_n$ or $|Zn|$ which is the resistive or impedance noise and is equal to $V_n/I_n$. The output 13 is effectively indicative of the overall rate of corrosion.

The illustrated structure provides effectively four outputs, each of which varies in a manner that is indicative of the rate and/or nature of the corrosion attack to which the electrodes 1, 2 and 3 are exposed. It has now been realized that in accordance with the present invention if a comparison is made between the signals appearing on outputs 9 and 11 that comparison yields important information as to the nature of the corrosion attack. Accordingly in accordance with the present invention a comparator circuit 14 is connected to outputs 9 and 11 and provides on output 15 an output signal which is representative of $I_n/I_{mean}$.

Output 15 results from the comparison of the mean (or dc) coupling current ($I_{mean}$) to the rms or standard deviation values of the electrochemical current noise ($I_n$), and is indicative of the degree or otherwise of the localised behaviour during corrosion attack. That is, a low value of the ratio $I_n:I_{mean}$ is indicative of general corrosion, whilst high values of the ratio are indicative of localised corrosion. More specifically, a ratio of greater than 1 is indicative of complete localised corrosion during pitting. The following relationships have been found to apply:

| | |
|---|---|
| $0.001 < I_n/I_{mean} < 0.01$ | General Corrosion |
| $0.01 < I_n/I_{mean} < 0.1$ | Mixed Corrosion |
| $0.1 < I_n/I_{mean} < 1.0$ | Localised Corrosion |
| $1.0 < I_n/I_{mean}$ | Initiation of pits |

It should be stressed that, in accordance with the present invention, no dc or ac potentials are applied between the electrodes and accordingly measurements are conducted under the natural conditions. This is a fundamental distinction between the present invention and prior art systems in which it has been known to apply a dc current at constant potential via a potentiostat to an electrode array and then to look at variations in the applied current resulting from electrochemical corrosion effects.

A further circuit 16 is provided which compares the output 13 (overall corrosion rate) with the output 15 (degree to which corrosion is localised) and produces an output 17 which is indicative of the rate of localised corrosion. Thus, the information yielded from application of the present invention in combination with information available from the various outputs provided in the arrangement illustrated in the accompanying drawing makes it possible to accurately determine both the rate and nature of a particular corrosion process.

Further equations relevant to an understanding of the present invention are set out below. In these equations the following terms are used:

$V_n$: Electrochemical Potential Noise (volts)
$I_n$: Electrochemical Current Noise (amps)
$I_{mean}$: Coupling Current—Mean (ZRA) (amps)
$R_n$: Resistance Noise = $V_n/I_n$ (ohm)
$I_{corr}$: Corrosion Current (amps)
$|Zn|$: Complex impedance (ohm) derived from $V_n/I_n$
$k, k_1, k_2$, Constants (a) Corrosion Rate The corrosion rate may be described by each of the two following equations:

$$I_{corr}=k_2/R_n=k_2I_n/V_n=k_2/|Z_n|$$

$$I_{corr}=k_1 I_{mean}$$

Thus an improved estimate of $I_{corr}$ is given by $$I_{corr} = \sqrt{\frac{k\, I_n\, I_{mean}}{V_n}} \quad \text{(Geometric mean of two systems)}$$

where $k=k_1 k_2$ (b) Corrosion Type $$\theta = \frac{\log(I_{mean}/I_n)}{k_3}$$

$\theta=1$ General corrosion
$\theta=0$ Pure localised corrosion
$k_3$ System dependent constant (c) Penetration Rate $I_{corr}$ as calculated in (a) gives average corrosion across electrode surface in order to calculate Penetration Rate (X).

$$X = \frac{I_{corr}}{A\,\theta}$$

where A is electrode area and $\theta$ is 'active surface ratio' as calculated in (b).

In all cases constants are determined experimentally.

(d) An alternative approach is as follows

Monitor $I_x(I_{mean})$, $I_n$, $V_{DC}(V_{mean})$, $V_n$

For general attack ratio $$\frac{I_n}{I_{DC}}$$

is small, estimate lower limit to be approx $10^{-3}$.

For pitting corrosion, single pits $$\frac{I_n}{I_{DC}} \approx 1,$$

(can be greater than 1). particularly if the fluctuations occur around zero — this is uncommon but is related to initiation and propogation of fresh pits.

Normally calculate polarisation resistance from correlated potential and current signals, for noise say $$\frac{V_n}{I_n} = R_p \quad \text{(ohm)}$$

Standard practice to correct for area of specimen and to normalise to $A.cm^{-2}$.

$$A_{(total)} \times \frac{V_n}{I_n} = R_p\, \Omega \cdot cm^2$$

To correct for area being attacked, modify A $$A_{(real)} = A_{(total)} \times \frac{I_{DC}}{I_n} \times 10^{-3}$$

$$\left(\text{i.e. if } \frac{I_n}{I_{DC}} = 10^{-3};\ A_{(real)} = A_{(total)},\ \text{etc.}\right)$$

$$R_{p(real)} = A_{(total)} \times \frac{I_{DC}}{I_n^2} \times 10^{-3} \times V_n \cdot \Omega \cdot cm^2$$

and $$i_{corr} = B\left(\frac{I_n^2}{A_{(total)} \times I_{DC} \times 10^{-3} \times V_n}\right) \text{amps cm}^{-2}$$

But $V_n \propto B\left(\frac{B}{V_n} = K\right)$ $$i_{corr} = k\left(\frac{I_n^2}{A_{(total)} \times I_{DC} \times 10^{-3}}\right) \text{amps cm}^{-2}$$

k depends on frequency at which measurements taken, but for "standard" pitting can approximate to $3\times 10^3$ (by assuming $V_n = 10\ \mu V$ when $B=30$ mV).

$$i_{corr} = 3 + 10^6\left(\frac{I_n^2}{A_{(total)} \times I_{DC}}\right) \text{amps cm}^{-2}$$

now $\frac{I_n}{I_{DC}}$ = coefficient of variation C $$i_{corr} = 3 + 10^6\left(\frac{I_n \times C}{A_{(total)}}\right)$$

Measuring $I_n$ and $I_{DC}$ and knowing A calculate penetration rates
e.g. $I_n = 10^{-9}$ Amps
$A = 10\ cm^2$
$C = 1$ $$i_{corr} = \frac{3 \times 10^6 \times 10^{-9} \times 1}{10}$$

Pitting
$= 3 \times 10^{-4}$ Amps $cm^2$ (at pit)
$= 300\ \mu A\ cm^{-2}$ ($+i_{DC} \sim 10^{-9}$ Amps)
$\simeq 150$ mpy (for steel)
$I_n = 10^{-9}$
$A = 10$
$C = 10^{-3}$ Uniform $i_{corr} = \frac{3 \times 10^6 \times 10^{-9} \times 10^{-3}}{10}$ $= 3 \times 10^{-7}$
$= 0.3\ \mu A\ cm^{-2}$
$\simeq 0.15$ mpy for steel e.g. $I_n = 10^{-7}$ Amps
$A = 10\ cm^2$
$C = 0.1$ $$i_{corr} = \frac{3 \times 10^6 \times 10^{-7} \times 0.1}{10}$$

$= 3 \times 10^{-3}$ amps $cm^{-2}$
$\simeq 1500$ mpy (for steel)
$I_{DC} \simeq 10^{-6}$ amps Uniform $C = 10^{-3}$, $i_n = 10^{-7}$, $A = 10$ -continued $i_{corr}$ $3 \times 10^{-5}$ amps cm$^{-2}$
15 mpy
$I_{DC} = 10^{-4}$ amps
$I_{DC} > \frac{1}{3} i_{corr}$

We claim:

1. An apparatus for detecting localised corrosion of a metallic surface, comprising an array of two or more electrodes fabricated from the same material as the metallic surface and exposed to the same corrosion conditions as the metallic surface, means for measuring the coupling current between two or more electrodes of the array, means for measuring electrochemical current noise originating in the electrode array, and means for comparing the coupling current with the electrochemical current noise to provide an output indicative of the degree to which corrosion is localised.

2. An apparatus according to claim 1, comprising two electrodes, a zero resistance ammeter connected between the two electrodes and providing an output corresponding to the dc coupling current between the electrodes, an electrochemical current noise measuring apparatus connected to the output of the zero resistance ammeter and providing an output corresponding to the current noise, and a comparator connected to the outputs of the zero resistance ammeter and the electrochemical current noise measuring apparatus and providing an output corresponding to the relative magnitudes of the dc coupling current and the current noise.

3. An apparatus according to claim 2, comprising an electrochemical potential noise measuring apparatus connected between the said two or more electrodes and a further electrode, a second comparator connected to the outputs of the electrochemical potential noise measuring apparatus and the means for measuring the electrochemical current noise, and a third comparator connected to the output of the second comparator and the said output indicative of the degree to which corrosion is localised.

4. An apparatus according to claim 1, comprising means for measuring the electrochemical potential noise originating in the electrode array, means for correlating the electrochemical potential noise and the electrochemical current noise to provide a resistive/ impedance noise related output, and means for comparing the said output indicative of the degree to which corrosion is localised with the resistive/impedance noise output to provide an output indicative of the rate of localised corrosion.

5. A method for detecting localised corrosion of a metallic surface, wherein an array of electrodes fabricated from the same material as the metallic surface is exposed to the same corrosion conditions as the metallic surface, the coupling current between two electrodes of the array is measured, electrochemical current noise originating in the electrode array is measured, and the coupling current is compared with the electrochemical current noise to provide an output indicative of the degree to which corrosion is localised.

6. A method according to claim 5, wherein the electrochemical potential noise originating in the electrode array is measured, the resistive/impedance noise is measured by comparison of the electrochemical current noise with the electrochemical potential noise, and the resistance/impedance noise is compared with the second output indicative of localised corrosion to provide an output indicative of the rate of localised corrosion.

* * * * *